US009433255B2

(12) United States Patent
Fanchiang et al.

(10) Patent No.: US 9,433,255 B2
(45) Date of Patent: Sep. 6, 2016

(54) STANCE-CONTROLLED ARTICULATED ANKLE-FOOT ORTHOSIS

(71) Applicant: Georgia State University Research Foundation, Inc., Atlanta, GA (US)

(72) Inventors: Hsin-Chen Daniel Fanchiang, Atlanta, GA (US); Mark Daniel Geil, Kennesaw, GA (US); Toshiki Nashimoto, Kowloon (HK)

( * ) Notice: Subject to any disclaimer, the term of this patent is extended or adjusted under 35 U.S.C. 154(b) by 231 days.

(21) Appl. No.: 14/057,034

(22) Filed: Oct. 18, 2013

(65) Prior Publication Data

US 2014/0109443 A1 Apr. 24, 2014

Related U.S. Application Data

(60) Provisional application No. 61/715,800, filed on Oct. 18, 2012.

(51) Int. Cl.

| | |
|---|---|
| ***A43B 7/14*** | (2006.01) |
| ***A61F 5/00*** | (2006.01) |
| ***A43B 7/20*** | (2006.01) |
| ***A61F 5/01*** | (2006.01) |

(52) U.S. Cl.

CPC . *A43B 7/14* (2013.01); *A43B 7/20* (2013.01); *A61F 5/0127* (2013.01)

(58) Field of Classification Search

CPC ........ A43B 7/20; A43B 7/14; A43B 7/1415; A61F 5/0127; A61F 5/01; A61F 5/0102

USPC .......................................................... 36/140

See application file for complete search history.

(56) References Cited

U.S. PATENT DOCUMENTS

| | | | | |
|---|---|---|---|---|
| 5,328,444 A * | 7/1994 | Whiteside | A61F 5/0127 | 16/375 |
| 5,778,563 A * | 7/1998 | Ahlbaumer | A43B 5/00 | 36/140 |
| 6,350,246 B1 * | 2/2002 | DeToro | A61F 5/0127 | 128/882 |
| 6,929,614 B1 * | 8/2005 | Jackovitch | A61F 5/0127 | 602/16 |
| 7,018,350 B2 * | 3/2006 | Hinshon | A61F 5/0127 | 602/16 |
| 7,112,181 B1 * | 9/2006 | DeToro | A61F 5/0127 | 602/27 |
| 7,867,184 B2 * | 1/2011 | Mitchell | A61F 5/0111 | 128/882 |
| 8,075,635 B2 * | 12/2011 | Orlandi | C11D 3/0021 | 510/276 |
| 8,221,341 B1 * | 7/2012 | Al-Oboudi | A61F 5/0127 | 36/103 |
| 2005/0148914 A1 * | 7/2005 | Currier | A61F 5/0127 | 602/5 |
| 2010/0125229 A1 * | 5/2010 | Rudolph | A61B 5/1038 | 602/16 |

* cited by examiner

*Primary Examiner* — Jila M Mohandesi

(74) *Attorney, Agent, or Firm* — FisherBroyles, LLP; Anthony J. DoVale

(57) ABSTRACT

Devices, methods, and systems for an articulated ankle-foot orthosis with a selectively retractable stop are presented. The orthosis includes at least one of a foot mold, a shank mold, a forefoot sensor, a heel sensor, a stop, and a connecting mechanism. The stop is positioned between the foot mold and the shank mold, and the stop is selectively retractable between a closed position and a generally opposing open position that allows plantar flexion of the foot mold during the stance phase of a typical human gait cycle. The connecting mechanism is configured to move the stop from the closed position to the open position in response to a signal from the heel sensor indicating a heel-strike event. The connecting mechanism is also configured to move the stop from the open position back to the closed position in response to a signal from the forefoot sensor indicating a toe-off event.

20 Claims, 4 Drawing Sheets

LS
100
180
185
210
200
150
322
352
320
332
354
350
370a
330
300
520
324
370b
420
310
LF
120
140
334
530
130
340
430
160
540
510
500
440
410
400
380

STANCE-CONTROLLED ARTICULATED ANKLE-FOOT ORTHOSIS

CROSS REFERENCE TO RELATED APPLICATIONS

This application claims the benefit of and priority to U.S. Provisional Patent 61/715,800, filed Oct. 18, 2012, which is incorporated in its entirety in this document by reference.

BACKGROUND

The following disclosure relates generally to the field of orthoses and, more specifically, to an articulated ankle-foot orthosis controlled by the foot stance of the wearer.

Idiopathic toe walkers describes persons who walk without making heel contact during the initial contact phase of the gait cycle, yet have no signs of neurological, orthopaedic, or psychiatric diseases.

The existing conventional orthosis that is commonly prescribed for idiopathic toe walkers improves heel contact by restricting plantar flexion of the foot (downward rotation of the foot, relative to the ankle). Restricted plantar flexion, however, causes other problems and impedes the development of a normal walking gait. Without plantar flexion during the loading response period of the gait cycle, individuals have a smaller base of support, which limits the stability of their gait. Furthermore, without plantar flexion during the push-off period of the gait cycle, individuals cannot generate sufficient propulsion to advance the body efficiently. These limitations contribute to reports by wearers that the conventional ankle-foot orthosis is uncomfortable, significantly impairs walking, and produces dissatisfactory results. Motorized ankle-foot orthoses offer increased motion control, but are too complicated, expensive, bulky, and heavy for widespread use.

Accordingly, there is a need for improved ankle-foot orthoses that encourage a normal gait while providing stability, efficient propulsion, comfort, and improved clinical results.

SUMMARY

An ankle-foot orthosis, according to various embodiments, comprises at least one of a foot mold, a shank mold, a forefoot sensor, a heel sensor, a stop, and a connecting mechanism. The foot mold can be connected to the shank mold by a flexible connector. The forefoot sensor can be positioned on a sole of the foot mold and near a distal end of the foot mold. The heel sensor can be positioned on the sole and a proximal end of the foot mold. The stop can be selectively positioned between the foot mold and the shank mold. In one aspect, the stop is selectively retractable between a closed position that restricts plantar flexion of the foot mold, and a generally opposing open position that allows plantar flexion of the foot mold. The connecting mechanism can be positioned along a side wall of the foot mold. The connecting mechanism can be configured to move the stop about and between the closed position and the open position in response to at least one signal received from the forefoot sensor and/or the heel sensor. For example, the connecting mechanism can be configured to move the stop from the closed position to the open position in response to a signal from the heel sensor indicating a heel-strike event. In another example, the connecting mechanism can be also configured to move the stop from the open position back to the closed position in response to a signal from the forefoot sensor indicating a toe-off event.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE DRAWINGS

Reference will now be made to the accompanying drawings, which are not necessarily drawn to scale, and wherein.

DETAILED DESCRIPTION OF VARIOUS EMBODIMENTS

Figure 1:
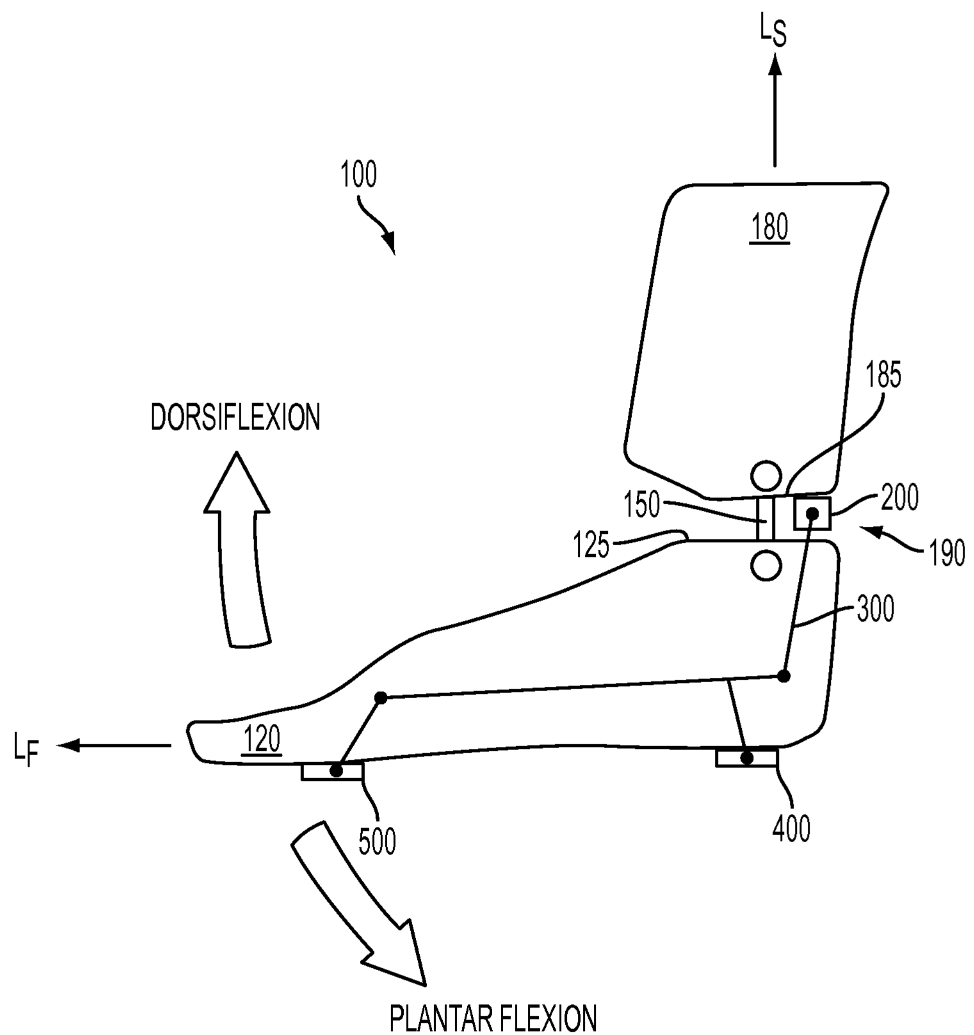
FIG. 1 is a side-view illustration of an orthosis and a schematic connecting mechanism, according to various embodiments.

The present systems and apparatuses and methods are understood more readily by reference to the following detailed description, examples, drawing, and claims, and their previous and following descriptions. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching in its best, currently known embodiment. To this end, those skilled in the relevant art will recognize and appreciate that many changes can be made to the various aspects described herein, while still obtaining the beneficial results of the technology disclosed. It will also be apparent that some of the desired benefits can be obtained by selecting some of the features while not utilizing others. Accordingly, those with ordinary skill in the art will recognize that many modifications and adaptations are possible, and may even be desirable in certain circumstances, and are a part of the invention described. Thus, the following description is provided as illustrative of the principles of the invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator. Thus, for example, the tip or free end of a device may be referred to as the distal end, whereas the generally opposing end or far end may be referred to as the proximal end.

Ranges can be expressed herein as from “about” one particular value, and/or to “about” another particular value. When such a range is expressed, another aspect includes from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

As used herein, the terms “optional” or “optionally” mean that the subsequently described event or circumstance may or may not occur, and that the description includes instances where said event or circumstance occurs and instances where it does not. As used herein, the term “facilitate” means to make easier or less difficult and the term “impede” means to interfere with, hinder, or delay the progress.

Although the various embodiments are described with reference to a human ankle and foot, the assemblies and methods described herein can be used with any of a variety of joints and in other vertebrates.

Plantar flexion is a downward rotation of the foot relative to the ankle. Dorsiflexion is an upward rotation of the foot. Plantar flexion and dorsiflexion are illustrated in FIG. 1. The shank is that part of the leg between the ankle and the knee in humans, or a corresponding part in other vertebrates.

FIG. 1 is an illustration of a two-part articulated ankle-foot orthosis 100 according to various embodiments. The orthosis 100 can comprise a foot mold 120 configured to be worn on at least a portion of the foot of a user, and a shank mold 180 configured to be worn on at least a portion of the leg of a user. In one aspect, the foot mold and the shank mold can be connected together but separated from each other by a predetermined distance. That is, an upper portion 125 of the foot mold 120 can be spaced from a lower portion 185 of the shank mold a predetermined distance such that a gap 190 is defined between the foot mold and the shank mold. In another aspect, the foot mold 120 and the shank mold 180 can be connected together by a connector 150. For example, the connector can be a flexible connector.

Figure 3:
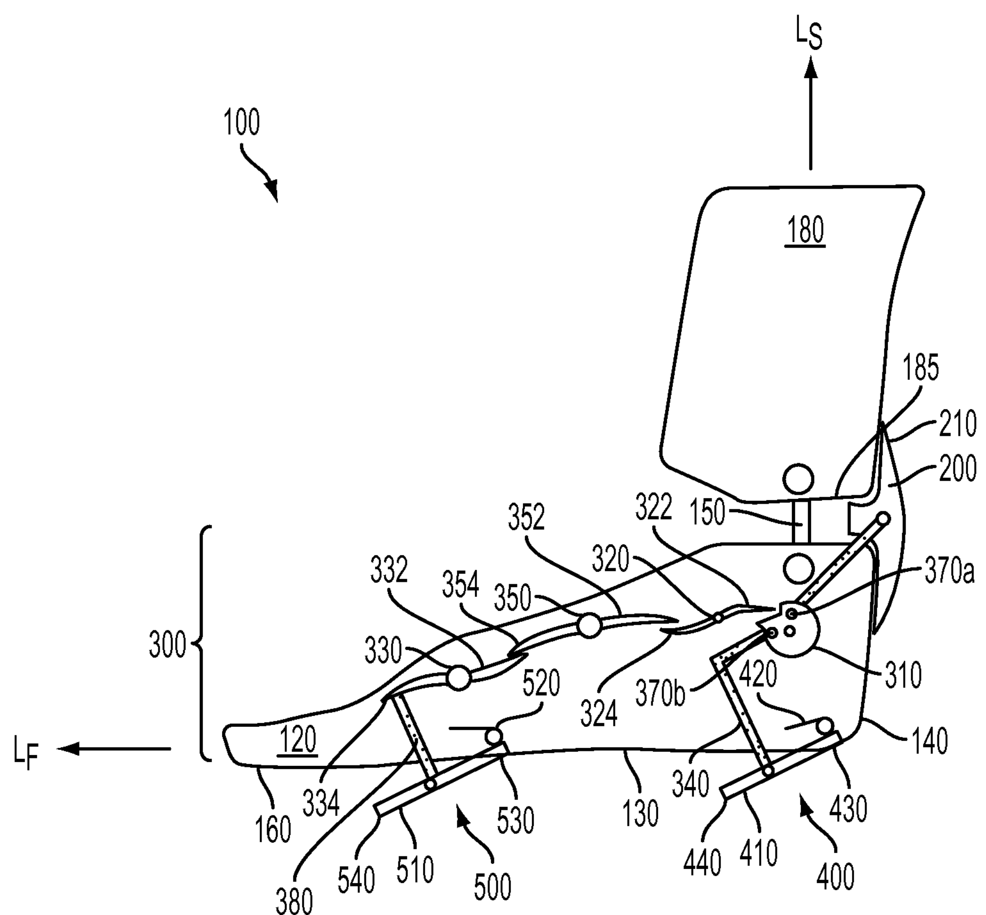
FIG. 3 is a side-view illustration of an orthosis including a connecting mechanism, according to a first embodiment.

In one aspect, the foot mold 120 can be sized and shaped to create a bed for a foot of a user. Optionally, the foot mold can be sized and shaped to create a bed for feet of a variety of shapes and sizes, or the foot mold can be custom-made. With reference to FIGS. 1 and 3, the foot mold can comprise a sole 130 configured to engage a walking surface or the shoe of a user, a longitudinal axis $L_F$, a proximal end 140 configured to be positioned adjacent the heel of a user when the orthosis is worn, and an opposed distal end 160 configured to be positioned adjacent the toe of a user when the orthosis is worn. In a further aspect, the shank mold 180 can be sized and shaped to engage a leg of the user. Optionally, the shank mold can be sized and shaped to engage legs having a variety of shapes and sizes, or the shank mold 180 can be custom-made. The shank mold can have a longitudinal axis $L_S$ as illustrated in FIGS. 1 and 3.

Figure 2:
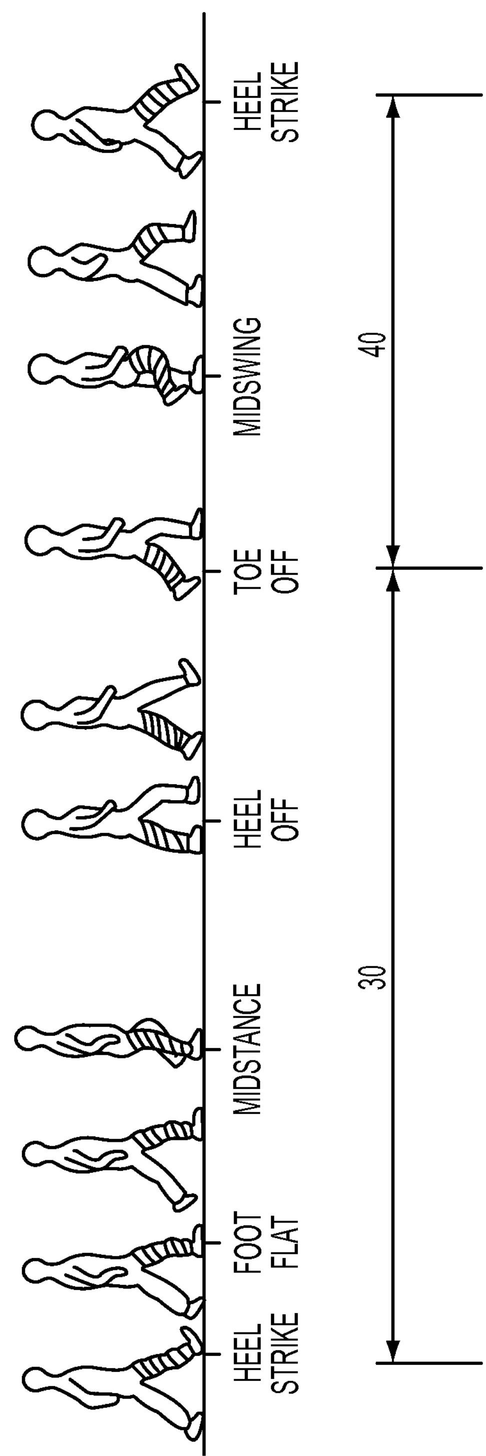
FIG. 2 is a graphical illustration of a typical gait cycle, with notes about the operation of an orthosis relative to the gait cycle, according to various embodiments.

Referring to FIG. 2, the human gait can be described using a number of phases or events, as shown. The stance phase 30 begins with an initial contact or heel strike on the walking surface. The stance phase 30 ends at toe-off; the event during which the toe leaves the ground and begins the swing phase 40. The swing phase 40 ends at the next heel strike.

As described more fully below, the orthosis 100 allows a user plantar flexion during the stance phase 30 which facilitates normal ankle rotation and improves stability and propulsion power. In one aspect, the orthosis 100 can allow normal ankle rotation, with plantar flexion, during the stance phase. Thus, in the stance phase 30, the orthosis can allow the user to selectively alter the angle formed between the longitudinal axis $L_F$ of the foot mold and the longitudinal axis $L_S$ of the shank mold as desired. During the swing phase 40, however, when the foot is in motion above the walking surface, the orthosis 100 can limit ankle rotation in order to facilitate a proper heel strike. That is, in the swing phase, the orthosis 100 can prevent or restrict the user from selectively altering the angle formed between the longitudinal axis $L_F$ of the foot mold and the longitudinal axis $L_S$ of the shank mold beyond a predetermined angle.

With reference again to FIG. 1, in one aspect, the orthosis 100 comprises at least one of a heel sensor 400, a forefoot sensor 500, a stop 200 (positioned between the foot mold 120 and the shank mold 180), and a connecting mechanism 300 such as a linkage to connect at least a portion of these elements. In another aspect, the connecting mechanism can respond mechanically to changes in the heel and forefoot sensors 400, 500 during walking. The connecting mechanism 300 is shown schematically in order to illustrate the existence of connections between the heel sensor 400, the forefoot sensor 500, and the stop 200. As more fully described herein, the connecting mechanism 300 can comprise a variety of components.

The stop 200, as shown in FIG. 1, can restrict plantar flexion when “closed” or “in place” between the foot mold 120 and the shank mold 180. In use and as described more fully below, the stop 200 can restrict motion between the foot mold 120 relative to the shank mold 180. That is, the stop can prevent or restrict rotation of the longitudinal axis $L_F$ of the foot mold relative to the longitudinal axis $L_S$ of the shank mold. In operation, therefore, the connecting mechanism 300 can be configured to respond to changes in the heel and/or the forefoot sensors 400, 500 and either open or close the stop 200. When opened, the stop 200 can be retracted or otherwise withdrawn from the space between the foot mold and the shank mold 180. For example, the connecting mechanism 300 can facilitate opening of the stop 200 during the stance phase 30, and closing of the stop 200 during the swing phase 40.

FIG. 3 is a schematic illustration of the orthosis 100, according to one aspect. In this aspect, the orthosis 100 comprises the heel sensor 400, the forefoot sensor 500, the stop 200, and the connecting mechanism 300. The connecting mechanism couples the heel sensor, the forefoot sensor, and the stop 200 together such that position changes in the heel and forefoot sensors 400, 500 produce a desired position change in the stop 200. In another aspect, the connecting mechanism 300 can operate mechanically without motors or powered actuators.

In one aspect, the heel sensor 400 comprises a heel pedal 410 mounted on the sole 130 of the foot mold 120 near or adjacent to the heel or proximal end 140 of the foot mold. In another aspect, a first end 430 of the heel pedal can be coupled to the foot mold, and a second end 440 of the heel pedal 410 can be spaced from the first end. In still another aspect, the heel sensor can be biased about and between a closed heel position, in which the first end and the second end of the heel pedal are substantially adjacent to the sole of the foot mold, and an open heel position, in which one of the first end 430 and the second end 440 of the heel pedal 410 is spaced from the sole 130.

The heel pedal 410 can be hingedly attached to a portion of the foot mold, according to one aspect. In another aspect, the heel sensor 400 can be biased toward the open position by a heel spring 420 configured to urge the heel sensor 400 open when the heel spring is in a first, expanded position. That is, when the heel spring 420 is in the first, expanded position, the heel sensor can be open such that one of the first end 430 and the second end 440 of the heel pedal 410 can be spaced from the sole 130 of the foot mold 120 a predetermined distance. In one aspect, the heel spring can be located adjacent the heel sensor. For example and without limitation, the heel spring 420 can be positioned around the first end 430 of the heel sensor, or directly positioned against the heel pedal. Optionally, the heel spring 420 can be positioned in any position that urges the heel sensor 400 open when the heel spring is in the first, expanded position.

In one aspect, the heel sensor 400 can be positioned on the sole 130 of the foot mold 120 such that when the heel sensor is open, the first end 430 of the heel pedal 410 can be coupled to the foot mold, and the second end 440 of the heel pedal can be spaced from the sole of the foot mold a predetermined distance. That is, in this aspect, the heel sensor can open towards the distal end 160 of the orthosis, as illustrated in FIG. 3. Optionally, in another aspect, the heel sensor 400 can be positioned on the sole 130 of the foot mold 120 such that when the heel sensor is open, the second end 440 of the heel pedal 410 can be coupled to the foot mold, and the first end 430 of the heel pedal can be spaced from the sole of the foot mold a predetermined distance. That is, in this aspect, the heel sensor can open towards the proximal end 140 of the orthosis instead of towards the distal end 160, as illustrated in FIG. 3. It is also contemplated that the heel sensor 400 can be any type of sensor or switch capable of sensing changes in the position of the heel of the user.

In one aspect, the forefoot sensor 500 comprises a forefoot pedal 510 mounted on the sole 130 of the foot mold 120 near or adjacent to the toe or distal end 160 of the foot mold. In another aspect, a first end 530 of the forefoot pedal can be coupled to the foot mold, and a second end 540 of the forefoot pedal 510 can be spaced from the first end. In still another aspect, the forefoot sensor can be biased about and between a closed forefoot position, in which the first end and the second end of the forefoot pedal are substantially adjacent to the sole of the foot mold, and an open forefoot position, in which one of the first end 530 and the second end 540 of the forefoot pedal 510 is spaced from the sole 130.

The forefoot pedal 510 can be hingedly attached to a portion of the foot mold, according to one aspect. In another aspect, the forefoot sensor 500 can be biased toward the open position by a forefoot spring 520 configured to urge the forefoot sensor 500 open when the forefoot spring is in a first, expanded position. That is, when the forefoot spring 520 is in the first, expanded position, the forefoot sensor can be open such that one of the first end 530 and the second end 540 of the forefoot pedal 510 can be spaced from the sole 130 of the foot mold 120 a predetermined distance. In one aspect, the forefoot spring can be located adjacent the forefoot sensor. For example and without limitation, the forefoot spring 520 can be positioned around the first end 530 of the forefoot sensor, or directly positioned against the forefoot pedal. Optionally, the forefoot spring 520 can be positioned in any position that urges the forefoot sensor 500 open when the forefoot spring is in the first, expanded position.

In one aspect, the forefoot sensor 500 can be positioned on the sole 130 of the foot mold 120 such that when the forefoot sensor is open, the first end 530 of the forefoot pedal 510 can be coupled to the foot mold, and the second end 540 of the forefoot pedal can be spaced from the sole of the foot mold a predetermined distance. That is, in this aspect, the forefoot sensor can open towards the distal end 160 of the orthosis, as illustrated in FIG. 3. Optionally, in another aspect, the forefoot sensor 500 can be positioned on the sole 130 of the foot mold 120 such that when the forefoot sensor is open, the second end 540 of the forefoot pedal 510 can be coupled to the foot mold, and the first end 530 of the forefoot pedal can be spaced from the sole of the foot mold a predetermined distance. That is, in this aspect, the forefoot sensor can open towards the proximal end 140 of the orthosis instead of towards the distal end 160, as illustrated in FIG. 3. It is also contemplated that the forefoot sensor 500 can be any type of sensor or switch capable of sensing changes in the position of the forefoot of the user.

In one aspect, at least a portion of the stop 200 can be sized and shaped to be positionable in the gap 190 defined between the foot mold 120 and the shank mold 180. In another aspect, a shoulder portion 210 of the stop can be configured to engage the foot mold 120 and/or the shank mold 180 outside of the gap between the foot mold and the shank mold. In still another aspect, the stop can be positioned near the rear or posterior side of the ankle of the user when the orthosis 100 is being worn. That is, the stop 200 can be positioned near or adjacent to at least one of the proximal side of the foot mold 120 and the proximal side of the shank mold 180 as shown in FIGS. 1 and 3. Alternatively, however, the stop 200 can be positioned at any location that limits motion between the foot mold 120 and the shank mold 180. The stop 200 can be sized and shaped to substantially or partially fill the gap 190 between the foot mold and the shank mold such that, by filling the gap, motion of the foot mold 120 relative to the shank mold 180 can be limited.

Figure 5:
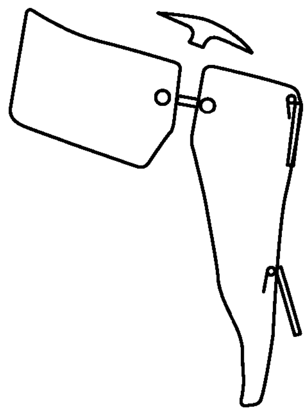
FIGS. 4-8 are side-view illustrations of an orthosis and its components, according to various embodiments, reacting to a progression of a foot through a typical gait cycle.
Figure 8:
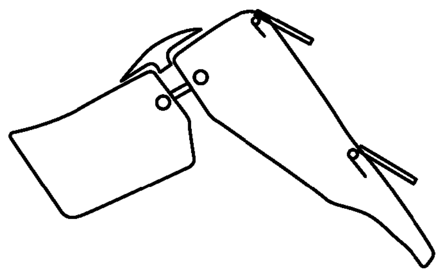
Figure 4:
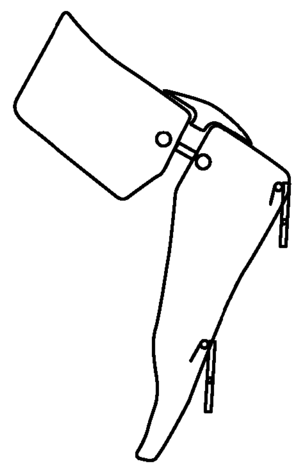
Figure 7:
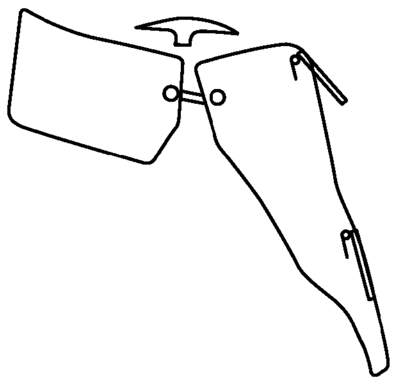
Figures 1, 3:
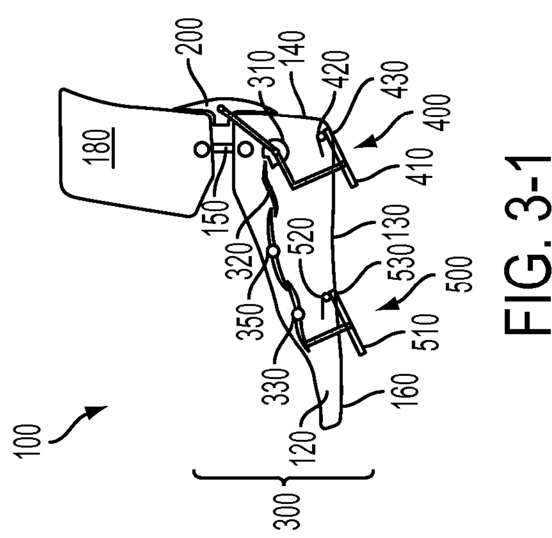
Figure 6:
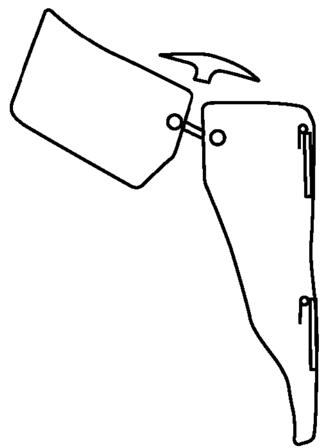

As described generally above, and more fully below, the stop 200 can be selectively movable from a closed position, in which at least a portion of the stop is positioned therein the gap 190 defined between the foot mold 120 and the shank mold 180 (as shown in FIGS. 3, 4, and 8), to an open position, in which the stop is retracted from the gap between the foot mold 120 and the shank mold 180 (as shown in FIGS. 5-7). As can be appreciated, when the stop 200 is retracted from the gap 190 (i.e., in the open position), the foot mold 120 can move relative to the shank mold 180. Further, when at least a portion of the stop is positioned in the gap between the foot mold and the shank mold (i.e., in the closed position), the foot mold 120 can be restricted from moving relative to the shank mold 180. In another aspect, the stop can be retractable by moving rearward, in a posterior direction, in order to open the space between foot mold 120 and the shank mold 180. In other aspects, the stop can be retractable up (toward the shank mold) or down (toward the foot mold), in order to clear the space between the foot mold 120 and the shank mold 180. For example, the stop 200 can be retractable in a manner that is similar to the barrel of a spring-mounted pen, such that the stop is retracted downward towards relative to the foot mold and out of the gap between the foot mold 120 and the shank mold 180.

In one aspect and as shown in FIG. 3, the connecting mechanism 300 comprises a plurality of linkages in order to mechanically control the position of the stop 200 in response to various positions of the heel sensor 400 and/or the forefoot sensor 500, without requiring the use of motors or powered actuators. At least one linkage of the plurality of linkages of the connecting mechanism 300 can be mounted to a side wall of the foot mold 120 or, in particular aspects, can be more integrated into the side wall of the foot mold 120 or otherwise protected from inadvertent damage and the elements.

The connecting mechanism 300, in one aspect, comprises at least one of a gear 310, a gear latch 320, a rotor 330, and an energy transferring linkage 350. In another aspect, the gear 310 can be connected by a fixed or rigid first linkage 340 to the heel sensor 400, and by a fixed or rigid second linkage 360 to the stop 200. The gear 310 can also be controlled in part by a gear latch 320. In operation, as described more fully below, the gear 310 can move the stop 200 in response to motion of at least the heel sensor 400. In one aspect, the first linkage 340 can be coupled eccentrically to the gear 310 so that motion of the lower linkage imparts rotation to the gear 310. Similarly, in another aspect, the second linkage 360 can be coupled eccentrically to the gear 310 so that rotation of the gear 310 imparts movement to the second linkage.

Still with reference to FIG. 3, in one aspect, the gear 310 can comprise at least two teeth 370*a*, 370*b*. When the gear latch 320 is in contact with the first gear tooth 370*a* (as illustrated in FIG. 3), the heel sensor 400 can be open (i.e., the second end 440 of the heel sensor can be spaced from the sole 130 of the foot mold 120) and the stop 200 can be closed (i.e., positioned in the gap 190 between the foot mold and the shank mold 180). When the heel sensor 400 is closed, the first linkage 340 rotates the gear 310 (clockwise in FIG. 3), and the rotating gear in turn moves the second linkage 360, which thereby moves the stop 200 to the open position (i.e., moved or retracted out of the gap between the foot mold and the shank mold.) In another aspect, the gear 310 can further comprise a gear spring configured to bias the gear. For example, the gear spring can be configured to bias the gear 310 in a counterclockwise direction, as shown in FIG. 3, such that the stop is engaged or in the closed position. Optionally, the gear spring can be configured to bias the gear in a clockwise direction.

In one aspect, the gear latch 320 can comprise a first member 322 configured to couple to or otherwise engage a portion of the gear 310, and a second member 324 configured to couple to or otherwise engage a portion of the energy transferring linkage 350. In one aspect, the gear latch 320 can further comprise a torsional spring or other biasing member such that the gear latch 320 is biased toward the gear teeth (i.e., clockwise in FIG. 3).

In one aspect, the energy transferring linkage 350 can be positioned at an intermediate location such that the energy transferring linkage transfers mechanical energy from the rotor 330 to the gear latch 320, as described below. In another aspect, the energy transferring linkage 350 can comprise a proximal arm 352 configured to couple to or otherwise engage a portion of the gear latch, and a distal arm 354 configured to couple to or otherwise engage a portion of the rotor. In use, energy imparted to the distal arm of the energy transferring linkage 350 from the rotor 330 can cause the energy transferring linkage to rotate and/or slide axially so that the proximal arm 352 of the energy transferring linkage 350 imparts this energy to the gear latch.

The rotor 330 can be a rotatable member coupled to both the forefoot sensor 500 and the gear 310 through the energy transferring linkage 350. In one aspect, the rotor can comprise a first arm 332 configured to couple to or otherwise engage a portion of the energy transferring linkage 350, and a second arm 334 configured to couple to or otherwise engage a portion of the forefoot sensor. In another aspect, mechanical energy from the forefoot sensor can be transferred through the rotor 330 to the energy transferring linkage. The rotor can optionally be positioned near or adjacent to the forefoot sensor 500. In another aspect, the rotor can be connected by a fixed or rigid third linkage 380 to the forefoot sensor. The forefoot sensor 500, as described above, can comprise the forefoot pedal 510 that is spring-biased toward the open position. In this aspect, the bias of the forefoot sensor 500, via the third linkage, can spring-bias the rotor 330 downward near its second arm 334 (i.e., counterclockwise in FIG. 3). In another aspect, the rotor can comprise one or more optional torsional springs or other biasing members to provide additional bias and stability to the rotor.

When the forefoot sensor 500 is open, as shown in FIG. 3, the rotor 330 can be in a neutral position and the first arm 332 of the rotor can be resting against a portion of the distal arm 354 of the energy transferring linkage 350. When the forefoot sensor 500 is closed, the third linkage 380 can rotate the rotor 330 (clockwise in FIG. 3), and the rotor 330 in turn allows the energy transferring linkage 350 to rotate (counterclockwise in FIG. 3). When the energy transferring linkage 350 rotates, it can transfer the mechanical energy from the rotor 330 to the gear latch 320, and move the gear latch such that the gear 310 moves from the second gear tooth 370*b* back to the first gear tooth 370*a*. This transfer to the first gear tooth, in turn, transfers a pulling force along the second linkage 360 and closes the stop 200 (i.e., moves the stop into the gap 190 between the foot mold 120 and the shank mold 180).

FIGS. 4 through 8 illustrate schematically the operation of the orthosis 100 described above. A smaller version of FIG. 3 is included as FIG. 3-1 along with FIGS. 4-8 for quick reference. In FIG. 4, the foot mold 120 is making initial contact with the floor or walking surface. At initial contact, the heel sensor 400 and the forefoot sensor 500 are open and the stop 200 is closed.

At or about the moment of heel strike, illustrated in FIG. 5, the heel sensor 400 moves to the closed position, thereby turning the gear 310 and opening the stop 200. Heel strike is a first event in the stance phase 30 (illustrated in FIG. 2) and marks the opening of the stop, thereby facilitating plantar flexion during the stance phase. As the gear 310 rotates and moves the stop 200 out of the gap 190 between the foot mold 120 and the shank mold 180, the first member 322 of the gear latch 320 becomes disengaged from its original position against the first gear tooth 370*a* of the gear 310. At a predetermined angular displacement of the gear latch relative to the longitudinal axis $L_F$ of the foot mold 120, the first member of the gear latch 320 can settle into or engage the second gear tooth 370*b* of the gear 310. The engagement of the second gear tooth 370*b* and the gear latch can keep the gear 310 in the desired position so that the second linkage 360 maintains the stop 200 in the open position. In one aspect, the predetermined angular displacement can be less than about 5 degrees, about 5 degrees, about 10 degrees, about 15 degrees, about 20 degrees, about 25 degrees, or greater than about 25 degrees.

FIG. 6 illustrates mid-stance, when the forefoot touches the walking surface, according to one aspect. In mid-stance, the heel sensor 400 remains closed, the forefoot sensor 500 closes and the stop 200 is open. Note that that the shank mold 180 is rotated slightly clockwise relative to the foot mold 120, indicating that the foot is in active plantar flexion at this point. That is, with the stop 200 in the open position, the angle formed between the longitudinal axis $L_F$ of the foot mold and the longitudinal axis $L_S$ of the shank mold can be changed as desired by a user of the orthosis 100, and in FIG. 6, the user has rotated the foot downward relative to the ankle. When the forefoot of the user touches the walking surface, the forefoot sensor 500 closes and rotates the rotor 330, which also allows the energy transferring linkage 350 to move. Notice that this rotation of the rotor 330 does not cause any reaction or change in position of the stop 200. Instead, because the rotor 330 can be spring-biased, rotation of the rotor creates a store of mechanical energy in the forefoot spring 520 and/or the rotor spring. Notice also that the rotation of the energy transferring linkage 350 does not cause any reaction or change in the position of the stop 200. The energy transferring linkage 350 can likewise be spring-biased, which means its rotation can also create an additional store of mechanical energy. Because the entire foot of the user engages the walking surface, the orthosis 100 can provide improved stability to the user during this phase of the gait cycle when compared to conventional orthotic devices.

At heel-off, illustrated in FIG. 7, the forefoot sensor 500 remains closed but the heel sensor 400 opens. When the heel sensor opens, the first linkage 340 exerts a force on a portion of the gear 310 causing the gear to rotate. The gear 310, however, is selectively locked into position by the gear latch 320. Unless and until the gear latch is moved, the gear 310 will not rotate.

At toe-off, illustrated in FIG. 8, the heel sensor 400 remains open and the forefoot sensor 500 opens. The opening of the forefoot sensor 500 releases the stored energy of the gear 310, the rotor 330, and/or the energy transferring linkage 350. This stored mechanical energy in the rotor 330, in the energy transferring linkage 350, and/or in the gear 310 is released substantially simultaneously. For example, the energy of the rotor 330 can trigger movement in the energy transferring linkage 350 which, in turn, strikes the second member 324 of the gear latch 320 and pushes the first member 322 of the gear latch out of the second gear tooth 370*b* of the gear 310, thereby releasing the gear. When the gear 310 is released, the gear rotates back (counterclockwise in FIG. 3) until the first member 322 of the gear latch engages a portion of the first gear tooth 370*a*. The movement of the gear 310 until the first member 322 of the gear latch 320 engages a portion of the first gear tooth 370*a* causes the stop 200 to move back into the closed position, in which at least a portion of the stop is positioned in the gap 190 between the foot mold 120 and the shank mold 180. In this aspect, the opening of the forefoot sensor 500, through the linkages in the connecting mechanism 300, causes the stop 200 to recoil back into its closed position.

After the position illustrated in FIG. 8, the stop 200 remains closed while the foot travels forward, through the swing phase 40 (illustrated in FIG. 2), until the foot once again makes initial contact with the walking surface (as shown in FIG. 4) and the process is repeated.

In use, in one aspect, the orthosis 100 can be worn as a shoe and the like. For example, a user could put his foot in the orthosis and use the orthosis in place of a shoe. Optionally, in another aspect, elements of the orthosis 100 could be added to a shoe. For example, at least one of the foot mold 180, the stop 200, the connecting mechanism 300, the heel sensor 400 and the forefoot sensor 500 could be added to the shoe of a user so that, when the shoe is worn along with a shank mold 180, the user of the device is selectively prevented from rotating his foot relative to his leg. In still another aspect, the orthosis 100 could be worn inside of a shoe. For example, the orthosis could be placed on the foot of a user, and the orthosis and foot could be inserted together inside of a shoe. In another aspect, elements of the orthosis could be formed integrally with a shoe. That is, at least one of the foot mold 180, the stop 200, the connecting mechanism 300, the heel sensor 400 and the forefoot sensor 500 could be formed integrally with a shoe, and the remaining elements of the orthosis could worn on the foot and/or leg of a user.

Although the assemblies and methods are described herein in the context of an articulated ankle-foot orthosis, the technology disclosed herein is also useful and applicable in other contexts. Moreover, although several embodiments have been described herein, those of ordinary skill in art, with the benefit of the teachings of this disclosure, will understand and comprehend many other embodiments and modifications for this technology. The invention therefore is not limited to the specific embodiments disclosed or discussed herein, and that can other embodiments and modifications are intended to be included within the scope of the appended claims. Moreover, although specific terms are occasionally used herein, as well as in the claims or concepts that follow, such terms are used in a generic and descriptive sense only, and should not be construed as limiting the described invention or the claims that follow.

What is claimed is:

1. An ankle-foot orthosis to be worn by a user walking on a walking surface, the orthosis comprising:

a foot mold configured to be worn on at least a portion of the foot of the user, the foot mold having a sole, a proximal end configured to be positioned adjacent a heel of the user when the orthosis is worn, an opposed distal end configured to be positioned adjacent a toe of the user when the orthosis is worn, and a longitudinal axis:

a shank mold having a longitudinal axis and configured to be worn on at least a portion of a leg of the user, wherein the shank mold is spaced from the foot mold such that a gap is defined between the foot mold and the shank mold, and wherein the shank mold is connected to the foot mold by a connector;

a forefoot sensor coupled to the sole substantially adjacent the distal end of the foot mold;

a heel sensor coupled to the sole substantially adjacent the proximal end of the foot mold;

a stop movable about and between a closed stop position, in which at least a portion of the stop is positioned in the gap between the foot mold and the shank mold, and an open stop position, in which the stop is retracted from the gap, wherein in the closed stop position, the foot mold is substantially restricted from moving relative to the shank mold, and wherein in the open stop position, the foot mold is movable relative to the shank mold; and a connecting mechanism coupled to the stop, the forefoot sensor and the heel sensor, wherein the connecting mechanism comprises a plurality of linkages to mechanically move the stop in response to a signal from at least one of the heel sensor and the forefoot sensor without the use of motors or powered actuators.

2. The orthosis of claim 1, wherein the connecting mechanism is configured to move the stop to the open stop position in response to a signal from the heel sensor, and wherein the connecting mechanism is configured to move the stop to the closed stop position in response to a signal from the forefoot sensor.

3. The orthosis of claim 1, wherein the connecting mechanism comprises a gear, a first linkage, and a second linkage, wherein the gear defines at least two teeth and is connected to the heel sensor by the first linkage, and wherein the gear is connected to the stop by the second linkage.

4. The orthosis of claim 3, wherein the first linkage and the second linkage are eccentrically connected to the gear.

5. The orthosis of claim 3, wherein the connecting mechanism further comprises a rotatable rotor and a third linkage, wherein the rotatable rotor is coupled to the gear, and wherein the rotatable rotor is connected to the forefoot sensor by the third linkage.

6. The orthosis of claim 5, wherein the connecting mechanism further comprises a gear latch, and wherein the rotatable rotor is coupled to the gear by the gear latch.

7. The orthosis of claim 6, wherein the gear latch is configured to engage the at least two teeth of the gear, and wherein the engagement of the gear latch and at least one tooth of the gear substantially prevents undesirable rotation of the gear.

8. The orthosis of claim 7, wherein the gear latch comprises a biasing member such that the gear latch is biased toward the at least two teeth of the gear.

9. The orthosis of claim 8, wherein the heel sensor comprises a heel pedal hingedly attached to the foot mold and a heel spring configured to bias the heel sensor from a closed heel position, in which a first and second end of the heel pedal are adjacent to the sole of the foot mold, to an open heel position, in which the second end of the heel pedal is spaced from the sole.

10. The orthosis of claim 9, wherein the forefoot sensor comprises a forefoot pedal hingedly attached to the foot mold and a forefoot spring configured to bias the forefoot sensor from a closed forefoot position, in which a first and second end of the forefoot pedal are adjacent to the sole of the foot mold, to an open forefoot position, in which the second end of the forefoot pedal is spaced from the sole.

11. The orthosis of claim 10, wherein when the heel sensor is in the closed heel position and the forefoot sensor is in the closed forefoot position, the stop is in the open stop position.

12. The orthosis of claim 10, wherein when at least one of the heel sensor and the forefoot sensor are in the respective closed position, the stop is in the open stop position.

13. The orthosis of claim 10, wherein when the heel sensor is in the open heel position and the forefoot sensor is in the open forefoot position, the stop is in the closed stop position.

14. The orthosis of claim 10, wherein the rotor comprises a biasing member, wherein movement of the forefoot pedal towards the closed forefoot position rotates the rotor, and wherein rotation of the rotor creates a store of mechanical energy in at least one of the forefoot spring and the rotor biasing member.

15. The orthosis of claim 14, wherein when the forefoot sensor moves to the open forefoot position, the store of mechanical energy is released and the gear latch releases the gear.

16. The orthosis of claim 1, wherein the orthosis is configured to be worn as a shoe of the user.

17. The orthosis of claim 1, wherein the orthosis is configured to be worn inside of a shoe of the user.

18. A method of selectively, substantially preventing movement of a foot of a user relative to a leg of the user when walking on a walking surface comprising:

providing an ankle-foot orthosis to be worn by the user comprising:

a foot mold configured to be worn on at least a portion of the foot of the user, the foot mold having a sole, a proximal end configured to be positioned adjacent a heel of the user when the orthosis is worn, an opposed distal end configured to be positioned adjacent a toe of the user when the orthosis is worn, and a longitudinal axis:

a shank mold having a longitudinal axis and configured to be worn on at least a portion of the leg of the user, wherein the shank mold is spaced from the foot mold such that a gap is defined between the foot mold and the shank mold, and wherein the shank mold is connected to the foot mold by a connector;

a forefoot sensor coupled to the sole substantially adjacent the distal end of the foot mold;

a heel sensor coupled to the sole substantially adjacent the proximal end of the foot mold;

a stop movable about and between a closed stop position, in which at least a portion of the stop is positioned in the gap between the foot mold and the shank mold, and an open stop position, in which the stop is retracted from the gap, wherein in the closed stop position, the foot mold is substantially restricted from moving relative to the shank mold, and wherein in the open stop position, the foot mold is movable relative to the shank mold; and a connecting mechanism coupled to the stop, the forefoot sensor and the heel sensor, wherein the connecting mechanism comprises a plurality of linkages to mechanically move the stop in response to a signal from at least one of the heel sensor and the forefoot sensor without the use of motors or powered actuators.

19. The method of claim 18, wherein the connecting mechanism is configured to move the stop to the open stop position in response to a signal from the heel sensor, and wherein the connecting mechanism is configured to move the stop to the closed stop position in response to a signal from the forefoot sensor.

20. The method of claim 18, wherein the orthosis is configured to be worn inside of a shoe of the user.

* * * * *